US010342557B2

(12) United States Patent
Youn et al.

(10) Patent No.: US 10,342,557 B2
(45) Date of Patent: Jul. 9, 2019

(54) INTRAVASCULAR DEVICE FOR REMOVING THROMBOSIS AND RECOVERING BLOOD FLOW

(71) Applicants: Sung-Won Youn, Daegu (KR); Young-Cheol Lee, Busan (KR)

(72) Inventors: Sung-Won Youn, Daegu (KR); Young-Cheol Lee, Busan (KR)

(73) Assignee: Korea Institute of Industrial Technology (KR)

( * ) Notice: Subject to any disclaimer, the term of this patent is extended or adjusted under 35 U.S.C. 154(b) by 126 days.

(21) Appl. No.: 15/512,718

(22) PCT Filed: Sep. 22, 2015

(86) PCT No.: PCT/KR2015/009906
§ 371 (c)(1),
(2) Date: Mar. 20, 2017

(87) PCT Pub. No.: WO2016/047986
PCT Pub. Date: Mar. 31, 2016

(65) Prior Publication Data
US 2017/0290599 A1    Oct. 12, 2017

(30) Foreign Application Priority Data
Sep. 23, 2014 (KR) .................. 10-2014-0126582

(51) Int. Cl.
*A61F 2/01*    (2006.01)
*A61B 17/221*    (2006.01)

(52) U.S. Cl.
CPC .............. *A61B 17/221* (2013.01); *A61F 2/01* (2013.01); *A61B 2017/2215* (2013.01); *A61F 2002/016* (2013.01)

(58) Field of Classification Search
CPC ...... A61F 2002/9505; A61F 2002/9511; A61F 2230/0069; A61F 2/01; A61F 2/90;
(Continued)

(56) References Cited

U.S. PATENT DOCUMENTS

2007/0093744 A1\* 4/2007 Elmaleh ........... A61B 17/22004
604/22
2008/0177301 A1\* 7/2008 Svensson .................. A61F 2/07
606/228

FOREIGN PATENT DOCUMENTS

KR    10-1999-0013858 A    2/1999
KR    10-2007-0063559 A    6/2007
(Continued)

OTHER PUBLICATIONS

International Search Report for PCT Application No. KR2015/009906 dated Dec. 11, 2015.

*Primary Examiner* — David C Eastwood
*Assistant Examiner* — Mohamed G Gabr
(74) *Attorney, Agent, or Firm* — Innovation Counsel LLP

(57) ABSTRACT

Disclosed herein is an intravascular device for removing thrombosis and recovering a blood flow, wherein the attachment of thrombosis can be facilitated since a plurality of minute protrusions are formed on the surface of the stent structure. The present inventive concept is able to significantly minimize any separation of the thrombosis when the device for removing thrombosis and recovering a blood flow is transferred to the outside of a human body in such a way that a plurality of minute protrusions are formed on the surface of the stent structure, and the attachment of the thrombosis to the stent can be facilitated.

9 Claims, 5 Drawing Sheets

(58) Field of Classification Search
CPC ............. A61F 2/95; A61M 2025/0019; A61M 2205/0244; A61M 2205/04; A61B 17/221; A61B 2010/0216; A61B 2017/22034; A61B 2017/22038; A61B 2017/320012; A61B 2090/701; A61B 10/02

See application file for complete search history.

(56) References Cited

FOREIGN PATENT DOCUMENTS

| | | |
|---|---|---|
| KR | 10-2009-0094587 A | 9/2009 |
| KR | 10-2014-0008315 A | 1/2014 |

* cited by examiner

INTRAVASCULAR DEVICE FOR REMOVING THROMBOSIS AND RECOVERING BLOOD FLOW

CROSS-REFERENCE TO RELATED APPLICATIONS

This application claims priority to and the benefit of PCT Patent Application PCT/KR2015/009906 filed in the Korean Intellectual Property Office on Sep. 22, 2015 which claims priority to and the benefit of Korean Patent Application No. 10-2014-0126582 filed in the Korean Intellectual Property Office on Sep. 23, 2014, the entire contents of which are incorporated herein by reference.

TECHNICAL FIELD

The present inventive concept relates to an intravascular device for removing thrombosis and recovering blood flow, and in particular to an intravascular device for removing thrombosis and recovering blood flood, which is disposed at a coronary artery, for example, a carotid artery, a vertebrobasilar artery, a middle cerebral artery, an anterior cerebral artery, a posterior cerebral artery, etc., arteries at other peripheral nerves, lesion portions of veins, thus removing any thrombosis to the outside which is narrowing or blocking a blood flow.

BACKGROUND ART

The stent for blood, in general, is a device which is used to improve a blood flow as it is inserted in a narrowed blood vessel and expands therein.

The typical stent for blood is designed to expand into a cylindrical shape after it has been inserted in a narrowed blood vessel, and remain permanently therein while curing the narrowed or blocked blood vessel.

The intravascular device used to remove thrombosis or cure a blocked blood vessel, however, has a stent shape or other shapes. It is configured to remove the thrombosis which is blocking a blood vessel after it has deployed at a lesion portion of a corresponding blood vessel. The aforementioned intravascular device, in general, is used to remove any thrombosis or impurities from a cerebral artery, a carotid artery, a vertebrobasilar artery, a coronary of a heart, peripheral arteries of legs and arms and veins corresponding thereto.

As an example, the Korean patent registration number 10-0960974 describes a device for improving a blood flow which includes a stent part configured in a cylindrical mesh shape and is able to artificially form a lumen inside a blood vessel which has been blocked or narrowed due to thrombosis, a narrow tubular part which becomes narrow in the direction of its front end so as to reduce a frictional force while accelerating a blood flow when the stent part is removed after it has been installed, and an extension part which is configured in such a way that it extends from one wire rod among the wire rods collected at a front end of the narrow tubular part so as to form a conical mesh structure of the narrow tubular part, and the other wire rods are cut by laser, thus forming a hook part at its tipped part. The extension part extends from the front end of the narrow tubular part and is attached, and is formed of the wire rods wherein the hook part is formed, and the narrow tubular part is formed short with a predetermined length corresponding to the outer diameter of the stent part of the cylindrical mesh structure, and the stent part, the narrow tubular part and the extension part are made of a metal material selected from the group consisting of a stainless steel, a stainless, and a nitinol, which is a shape-memory alloy.

Moreover, the Korean patent publication number 10-2012-0138975 describes a stent which can expand in a longitudinal direction. The aforementioned stent includes a plurality of struts which are formed in both ends of a cylindrical mesh shaped stent, and are arranged in a diagonal line shape and are configured to form a closed cell while allowing the closed cell to be formed in a spiral shape after it expands, and a plurality of link parts which are arranged in the center between the neighboring struts among a plurality of the struts and are connected and extend in a longitudinal direction. A plurality of the struts and a plurality of the link parts are integrally connected, and each strut which has expanded in the spiral shape, forms a diagonal line S-shape.

The conventional stent for removing thrombosis, however, is hard to collect and transfer the thrombosis. More specifically, the thrombosis may be easily separated from the thrombosis removing device during the transfer of the thrombosis to the outside after the thrombosis has been attached to a flat surface. The separated thrombosis may cause a stroke due to a new embolus at a cerebral artery which is different from the initial position of thrombosis. Moreover, the device may be disconnected during the operation, thus may cause another operation accident.

SUMMARY

Accordingly, it is an object of the present inventive concept to provide an intravascular device for removing thrombosis and recovering a blood flow, wherein a plurality of minute protrusions are formed on an inside of a stent which is able to remove thrombosis, which allows the thrombosis to be easily attached to the stent, thus preventing any separation of the thrombosis which might occur while the thrombosis removing device is transferred to the outside of a body.

To achieve the above object, there is provided an intravascular device for removing thrombosis and recovering a blood flow, which may include a plurality of protrusions formed on a body of a stent, thus facilitating the attachment of thrombosis.

In the present inventive concept, a plurality of minute protrusions are formed on the surface of an intravascular device for removing thrombosis and recovering a blood flow, and the attachment of the thrombosis to the stent is facilitated, and any separation of the thrombosis can be significantly prevented, wherein the separation of the thrombosis might occur while transferring the intravascular device for removing thrombosis and recovering a blood flow to the outside of a body.

According to an embodiment of the present disclosure, there is provided a stent for removing thrombosis and recovering a blood flow. The stent includes a body, the body having a mesh cylinder shape, and a plurality of protrusions which are formed on an inner surface of the body.

In an exemplary embodiment, the protrusions may extend toward a center of the stent from the body or extend obliquely toward a direction where the stents are withdrawn.

In an exemplary embodiment, the stent may further include a plurality of minute protrusions. Each of the plurality of minute protrusions may include a cylindrical core part, a plurality of pillar parts connected to the core part, and a plurality of mushroom shaped front end parts connected by the plurality of pillar parts to the cylindrical core part. Each of the plurality of mushroom shaped front end parts may include a circular tipped part and a sharp lateral part. The plurality of pillar parts may have a groove-shaped space disposed between the plurality of pillar parts to accommodate the thrombosis.

In an exemplary embodiment, the plurality of minute protrusions may overlap each other to form a multilayer structure.

In an exemplary embodiment, each of the plurality of minute protrusions may have a diameter of about 0.01 mm.

In an exemplary embodiment, the circular tipped part may minimize damage to a blood vessel wall, the thrombosis may move downward and reach the sharp lateral part of the plurality of minute protrusions with the aid of the pressing of the circular tipped part, the sharp lateral part may be configured to wrap and fix the thrombosis, thus enhancing the efficiency of the collection of the thrombosis, the thrombosis may contact with the circular tipped part or the lateral part of the plurality of minute protrusions as the stent expands, and the transformed thrombosis may pass through the sharp lateral part and reaches the groove-shaped space.

BRIEF DESCRIPTION OF THE DRAWINGS

The present inventive concept will become better understood with reference to the accompanying drawings which are given only by way of illustration and thus are not limitative of the present inventive concept, wherein.

DETAILED DESCRIPTION OF THE EMBODIMENTS

The present inventive concept is directed to an intravascular device for removing thrombosis and recovering a blood flow, wherein a plurality of protrusions are formed on the surface of a body of a stent, thus facilitating easy and strong attachment of thrombosis to the stent.

Moreover, the protrusions are formed on an inner surface of the body of the stent.

In addition, the protrusions are formed inclined in a direction where the stent is withdrawn.

Furthermore, the protrusions formed on the surface of the stent which corresponds to the intravascular device for removing thrombosis and recovering a blood flow are minute protrusions having small sizes, thus facilitating the attachment of the thrombosis to the stent.

Moreover, the minute protrusions may be formed of a cylindrical core part, a plurality of pillar parts which are connected in a radial direction with the core part, and a front end part connected to the pillars. The front end part is formed of a circular tipped part, and a sharp lateral part.

The present inventive concept will be described in detail with reference to the accompanying drawings.

Figure 1:
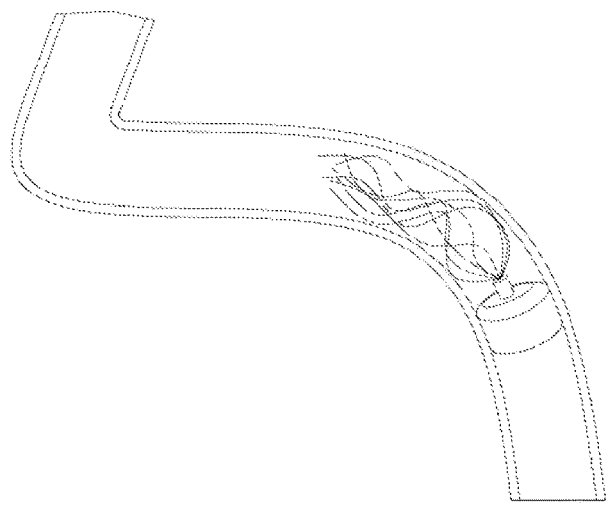
FIG. 1 is a view for describing a state where the thrombosis is being removed using a conventional stent for a cerebral blood vessel.
Figure 2:
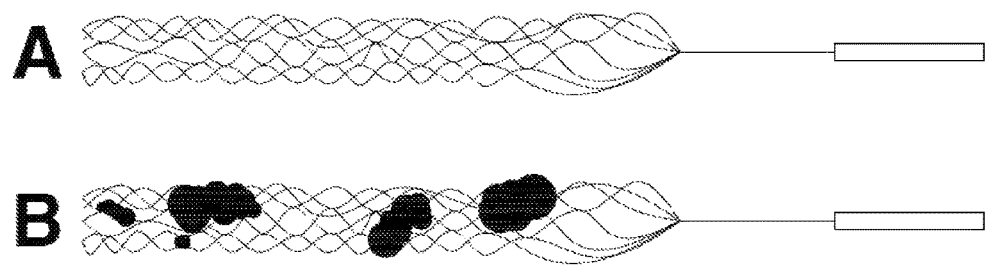
FIG. 2 is the comparison views before and after a thrombosis removing operation which has been carried using a conventional stent for a cerebral blood vessel.
Figure 3:
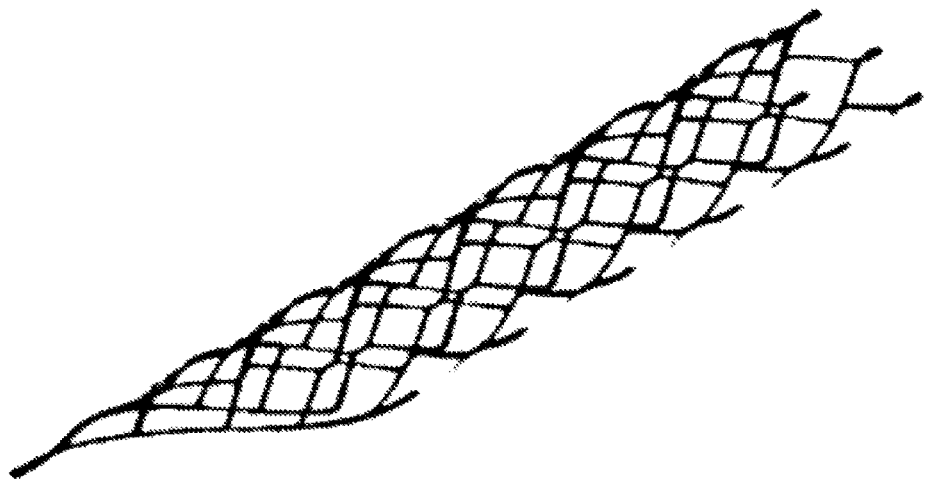
FIG. 3 is a perspective view illustrating a conventional stent for a cerebral blood vessel.
Figure 4:
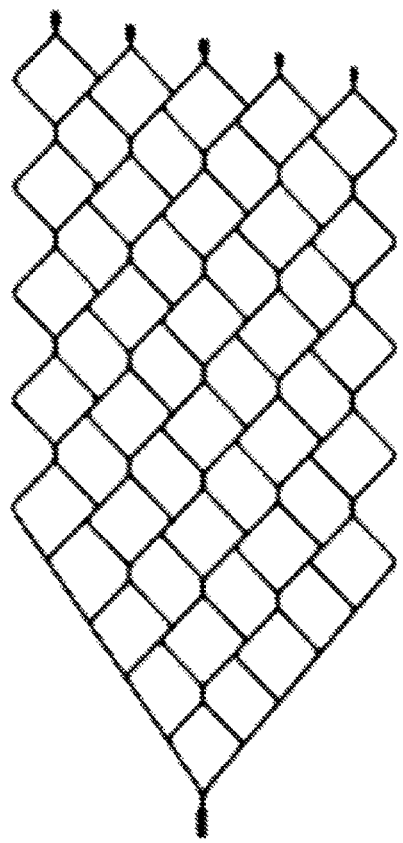
FIG. 4 is an exploded view illustrating a conventional stent for a cerebral blood vessel.
Figure 5:
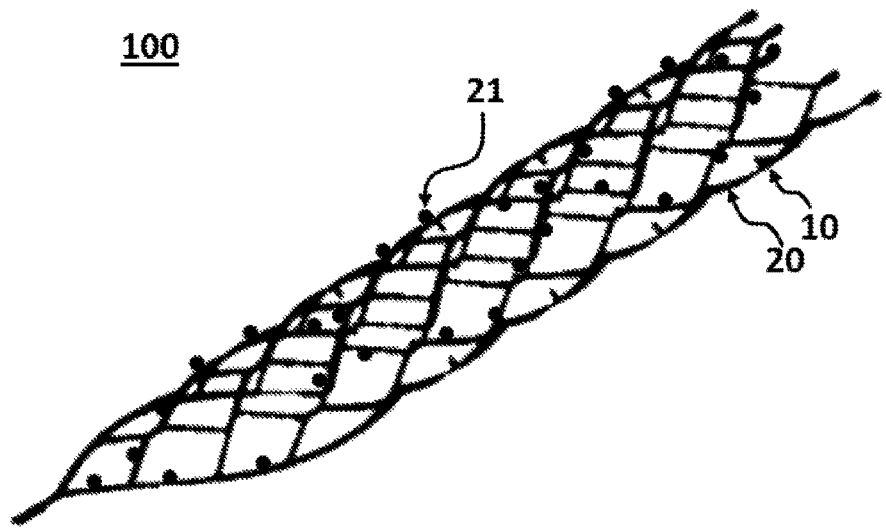
FIG. 5 is a perspective view illustrating an intravascular device for removing thrombosis and recovering a blood flow according to the present inventive concept.
Figure 6:
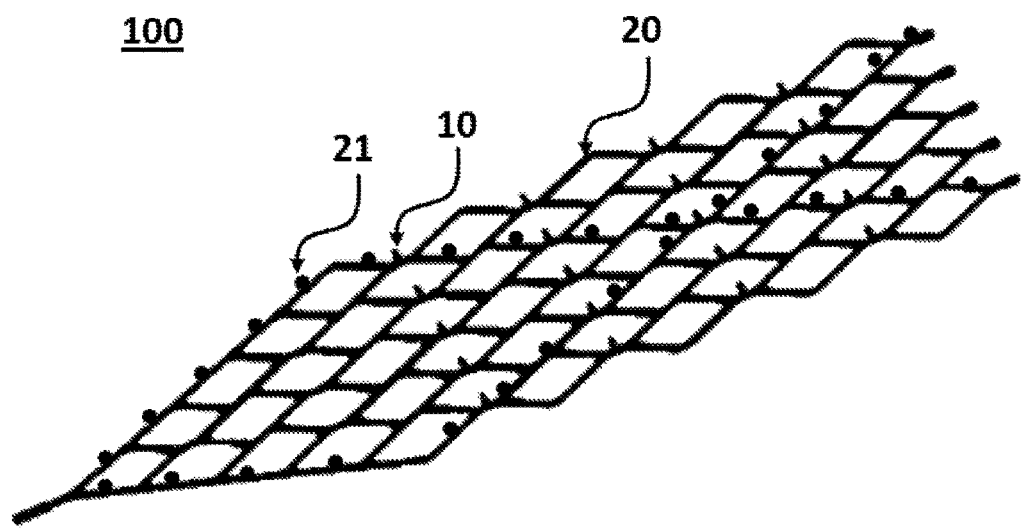
FIG. 6 is an exploded view illustrating an intravascular device for removing thrombosis and recovering a blood flow according to the present inventive concept.
Figure 7:
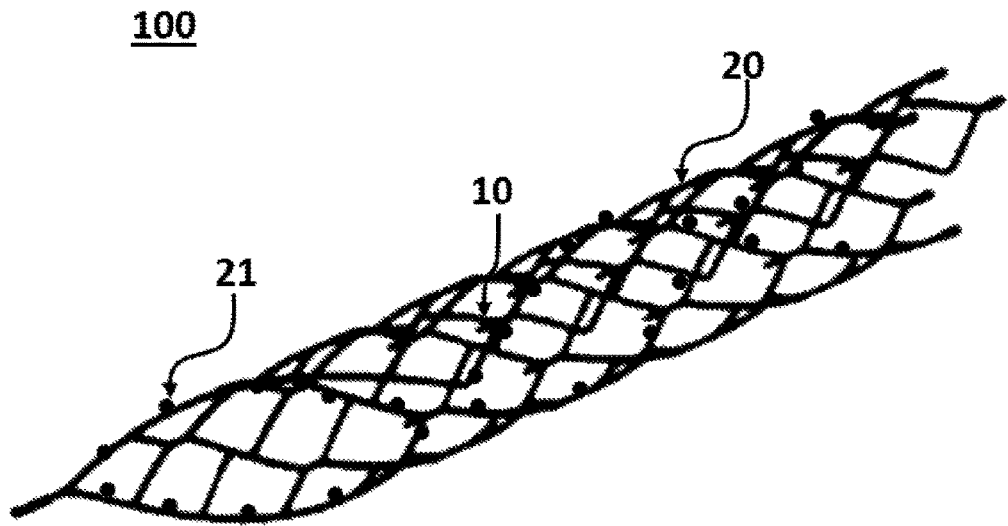
FIG. 7 is a perspective view illustrating an intravascular device for removing thrombosis and recovering a blood flow according to another embodiment of the present inventive concept.
Figure 8:
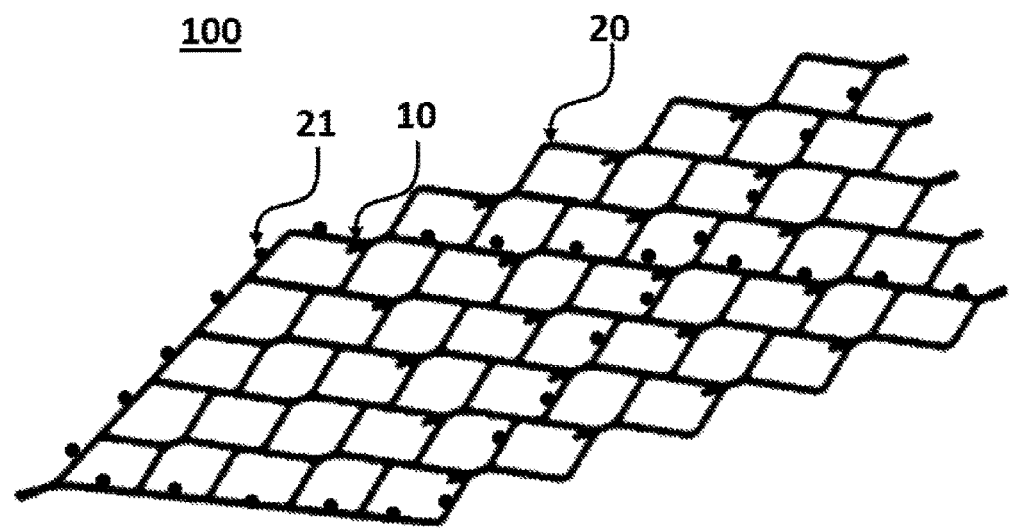
FIG. 8 is an exploded view illustrating an intravascular device for removing thrombosis and recovering a blood flow according to another embodiment of the present inventive concept.
Figure 9:
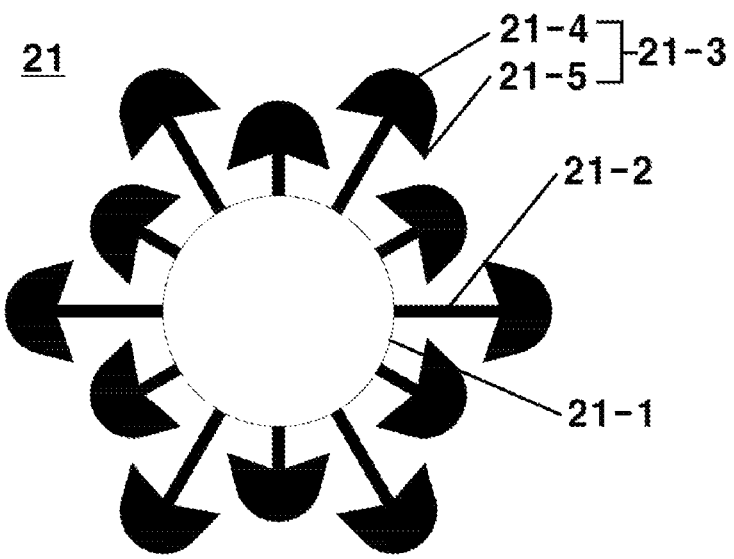
FIG. 9 is a detailed view illustrating minute protrusions according to the present inventive concept.
Figure 10:
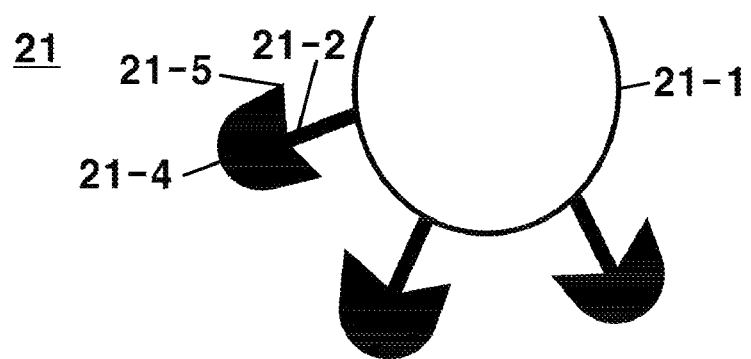
FIG. 10 is an enlarged view showing minute protrusions according to the present inventive concept.

FIG. 1 is a view for describing a state where the thrombosis is being removed using a conventional stent for a cerebral blood vessel. FIG. 2 is the comparison views before and after a thrombosis removing operation has been carried using a conventional stent for a cerebral blood vessel. FIG. 3 is a perspective view illustrating a conventional stent for a cerebral blood vessel. FIG. 4 is an exploded view illustrating a conventional stent for a cerebral blood vessel. FIG. 5 is a perspective view illustrating an intravascular device for removing thrombosis and recovering a blood flow according to the present inventive concept. FIG. 6 is an exploded view illustrating an intravascular device for removing thrombosis and recovering a blood flow according to the present inventive concept. FIG. 7 is a perspective view illustrating an intravascular device for removing thrombosis and recovering a blood flow according to another embodiment of the present inventive concept. FIG. 8 is an exploded view illustrating an intravascular device for removing thrombosis and recovering a blood flow according to another embodiment of the present inventive concept. FIG. 9 is a detailed view illustrating minute protrusions according to the present inventive concept. FIG. 10 is an enlarged view showing minute protrusions according to the present inventive concept.

The present inventive concept is able to facilitate the attachment of the thrombosis since the protrusions 10 are formed on the surface of the body 20.

The protrusions 10 may be formed inside the stent 100 for the sake of the attachment of thrombosis. The protrusions 10 may extent to the center of the stent 100 from the body 20. The protrusions 10 may be formed to incline to a direction where the stent 100 is withdrawn so that the thrombosis attached to the protrusions 10 does not easily separate when withdrawing the stent 100.

Moreover, the protrusions 10 are made of a synthetic resin, for example, silicon, PET, etc. which provides elasticity. Even though there is an obstacle, a cerebral blood vessel does not hurt since the protrusions 10 can be bent backwards due to elasticity.

The device for removing thrombosis and recovering a blood flow may be made of an alloy of platinum, nitinol, etc., and the whole parts of the aforementioned device may be made of a synthetic resin.

When operating, a guide conduit having a large diameter may be first inserted in the opening of a carotid artery or a vertebral artery, a coronary, peripheral nerves, and then the narrow conduit may be inserted in the guide conduit and is passed through a targeted blood vessel portion using a narrow conduit and a narrow steel wire, wherein the targeted blood vessel portion has been blocked by thrombosis. After the targeted blood vessel portion is passed using the narrow conduit, and the narrow steel wire is removed. The device of the present inventive concept is inserted in the narrow conduit and is pushed forward into the narrow conduit. When the device of the present inventive concept reaches an end portion of the narrow conduit, the narrow conduit is slowly moved backward and is peeled off while maintaining the position of the device of the present inventive concept. The cylindrical stent expands and spreads, thus keeping the thrombosis between the stent structure and the blood vessel wall. Here, the thrombosis may be attached to the contact surface between the thrombosis and the stent structure. As the stent structure is withdrawn, the attached thrombosis will enter into the inside of the conduit.

In the present inventive concept, the protrusions 10 may be formed on the surface of the body 20 of the stent 100 and may be inclined in the direction where the stent 100 is withdrawn. So, the narrow conduit and the stent can be collected into the inside of the guide conduit in a state where the thrombosis is kept between the protrusions and the narrow conduit in such a way to partially fold the stent by moving forward the narrow conduit unless they enter into the inside of the guide conduit in a state where the stent is unfolded by moving forward the narrow conduit.

In the present inventive concept, the minute protrusions 21 smaller than the protrusions 10 may be formed together on the surface of the body 20 of the stent 100 or may be formed alone, thus more easily facilitating the attachment of thrombosis. The shapes of the minute protrusions 21 will be described. Each minute protrusion 21 may include a cylindrical core part 21-1, and a pillar part 21-2 and a front end part 21-3 which includes a circular tipped part 21-4 and a sharp lateral part 21-5. The front end part 21-3 may have a mushroom shape and may be fixed to the core part 21-1 by the pillar part 21-2 which extends to a center of the core part 21-1 from the front end part 21-3. Each mushroom-shaped front end part 21-3 is formed of a circular tipped part 21-4, and a sharp lateral part 21-5. Given that the size of a red blood cell which has a circular plate shape like a donut is about 6-8 microns, it may be estimated that the size of the basic unit of the polymer of a fibrin might have the size which is similar with the aforementioned size.

For this reason, the minute protrusion 21 may have a diameter of about 0.01 mm. The aforementioned minute structure of the surface may safely and efficiently wrap and anchor the mesh structure of the fibrin polymer when the unit structure forming the stent contacts with the thrombosis during the operation stage, for example, a stent expansion, etc.

Moreover, the minute protrusions 21 may be formed on the surface to overlap each other to form a multilayer structure, for example, a two layer structure.

As compared to the one-layer structure, the multilayer structure may increase the number of the arrangements of the minute protrusions on the limited surface area of the stent structure, and the mesh structure of the fibrin polymer in the thrombosis can be easily wrapped by the multilayer structure and, thus, efficiency to remove the thrombosis can be increased.

The circular tipped part 21-4 of each minute protrusion 21 is rounded, thus minimizing any damage to the blood vessel wall during the operation.

The sharp lateral part of the minute protrusion has a similar structure with the lateral part of an arrowhead or the lateral part of a fish hook, by which the thrombosis of a fibrin polymer, etc. can be easily wrapped and fixed to the minute protrusion, thus, the collection efficiency of the thrombosis can be enhanced. When the thrombosis and the stent 100 contact with each other due to the expansion of the stent 100, the thrombosis might contact with the circular tipped part 21-4 and/or the sharp lateral part 21-5 of the minute protrusion 21. During operation, the deformed thrombosis might pass through the sharp lateral part 21-5 and might reach to the pillar of the minute protrusion. At this time, the thrombosis is wrapped and anchored to the sharp lateral part of the minute protrusion.

The pillar part 21-2 of the minute protrusion 21 may have a groove-shaped space disposed between the plurality of pillars to accommodate the thrombosis. The thrombosis may pass through the sharp lateral part 21-5 of the minute protrusion 21, so the thrombosis can be accommodated in the space of the pillar part 21-2 of the minute protrusion 21. The wrapping and anchoring represent that the thrombosis may move in the normal direction, namely, toward the core part 21-1 from the circular tipped part 21-4 of the minute protrusion 21. The movement of the thrombosis in the opposite direction is unavailable because the circular tipped part 21-4 may prevent the movement of the thrombosis to the opposite direction.

Since the circular tipped part having sharp lateral part 21-5 is able to stably fix the mesh structure (a fibrin polymer) of the thrombosis, the attachment of the thrombosis to the minute protrusion can be more stably carried out after the stent contacts the thrombosis. Since the thrombosis does not separate from the stent 100) when the stent 100 is withdrawn, the thrombosis can be effectively removed.

The present inventive concept, therefore, is able to significantly prevent any separation of the thrombosis from the stent when the stent is withdrawn. Because the minute protrusions are formed on the surface of the stent which is an intravascular device for removing thrombosis and recovering a blood flow, the attachment of the thrombosis to the stent is facilitated.

As the present inventive concept may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A stent for removing thrombosis and recovering a blood flow, comprising:
   a body, the body having a mesh cylinder shape;
   a plurality of protrusions which are formed on an inner surface of the body, and
   a plurality of minute protrusions formed on a surface of the body,
   wherein each of the plurality of minute protrusions includes a cylindrical core part, a plurality of pillar parts connected to the core part, and a plurality of mushroom shaped front end parts connected by the plurality of pillar parts to the cylindrical core part,
   wherein each of the plurality of mushroom shaped front end parts includes a circular tipped part and a sharp lateral part,
   wherein the plurality of pillar parts have a groove-shaped space disposed between the plurality of pillar parts to accommodate the thrombosis,
   wherein the plurality of minute protrusions include a plurality of first minute protrusions and a plurality of second minute protrusions, a length of the plurality of pillar parts in the plurality of first minute protrusions being a longer than a length of the plurality of pillar parts in the plurality of second minute protrusions, and wherein the plurality of mushroom shaped front end parts of the first minute protrusion overlap the plurality of mushroom shaped front end parts of the second minute protrusion in a plan view.

2. The stent of claim 1, where in the plurality of protrusions extend toward a center of the stent from the body.

3. The stent of claim 2, where each of the plurality of minute protrusions has a diameter of about 0.01 mm.

4. The stent of claim 3, wherein the circular tipped part minimizes damage to a blood vessel wall, wherein the minute projects are capable of moving the thrombosis downward to reach the sharp lateral part of the plurality of minute protrusions with the aid of the pressing of the circular tipped part, the sharp lateral part being configured to wrap and fix the thrombosis, thus enhancing the efficiency of the collection of the thrombosis, and wherein the circular tipped part or the lateral part of the plurality of minute protrusions is capable of contacting the thrombosis as the stent expands and transferring the thrombosis to the groove-shaped space through the sharp lateral part.

5. The stent of claim 1, wherein the protrusions extend obliquely toward a direction where the stent is withdrawn from a blood vessel.

6. The stent of claim 5, wherein the plurality of minute protrusions overlap each other to form a multilayer structure.

7. The stent of claim 6, where each of the plurality of minute protrusions has a diameter of about 0.01 mm.

8. The stent of claim 7, wherein the circular tipped part minimizes damage to a blood vessel wall, wherein the minute projects are capable of moving the thrombosis downward to reach the sharp lateral part of the plurality of minute protrusions with the aid of the pressing of the circular tipped part, the sharp lateral part being configured to wrap and fix the thrombosis, thus enhancing the efficiency of the collection of the thrombosis, and wherein the circular tipped part or the lateral part of the plurality of minute protrusions is capable of contacting the thrombosis as the stent expands and transferring the thrombosis to the groove-shaped space through the sharp lateral part.

9. The stent of claim 1, wherein the plurality of first minute protrusions and the plurality of second minute protrusions are alternatingly disposed.

* * * * *